United States Patent [19]

Santangelo et al.

[11] Patent Number: 5,407,956
[45] Date of Patent: Apr. 18, 1995

[54] 2-AMINO-1,2,3,4-TETRAHYDRONAPHTHA-LENE DERIVATIVES ACTIVE ON THE CARDIOVASCULAR SYSTEM, PROCESSES FOR THEIR PREPARATION AND PHARMACEUTICAL COMPOSITIONS CONTAINING THEM

[75] Inventors: Francesco Santangelo, Milan; Giorgio Bertolini, Sesto San Giovanni; Cesare Casagrande, Arese; Francesco Marchini, Lodi; Stefania Montanari, Milan; Claudio Semeraro, Bresso, all of Italy

[73] Assignee: Zambon Group S.p.A., Vicenza, Italy

[21] Appl. No.: 32,845

[22] Filed: Mar. 17, 1993

[30] Foreign Application Priority Data

Mar. 17, 1992 [IT] Italy .................. MI92A0608

[51] Int. Cl.$^6$ ............................. A61K 31/215
[52] U.S. Cl. ..................... 514/510; 514/114; 514/651; 560/134; 560/139; 560/190; 562/11; 564/354
[58] Field of Search ............... 560/134, 139, 190; 564/306, 15, 354; 562/11; 514/114, 651, 510

[56] References Cited

FOREIGN PATENT DOCUMENTS 0072061 2/1983 European Pat. Off. .
0142283 5/1985 European Pat. Off. .
0321968 6/1989 European Pat. Off. .

OTHER PUBLICATIONS

The Merck Index, *An Encyclopedia of Chemicals, Drugs, and Biologicals*, 11th Ed., (1989) p. 583.
Haralambos E. Katerinopoulos, et al, "Correlates in Pharmacostructures", *Structure-Activity Relationships for Dopamine Analogs: A Review*, vol. 12 No. 3 (1987) pp. 223–248.
Andrew Fitton et al, "Drug Evaluation" *Dopexamine hydrochloride: A Review of its Pharmacodynamic and Pharmacokinetic Properties and Therapeutic Potential in Acute Cardiac Insufficiency*, Drugs 39, (2) (1990) pp. 308–330.

*Primary Examiner*—José G. Dees
*Assistant Examiner*—Samuel Barts
*Attorney, Agent, or Firm*—Stevens, Davis, Miller & Mosher

[57] ABSTRACT

Derivatives of 2-amino-1,2,3,4-tetrahydronaphthalene and their use in therapeutic field are described.

The compounds are particularly useful in the treatment of arterial hypertension, cardiac decompensation and renal failure, in the treatment of peripheral arteriopathies and in cerebrovascular insufficiency.

8 Claims, No Drawings

2-AMINO-1,2,3,4-TETRAHYDRONAPHTHALENE DERIVATIVES ACTIVE ON THE CARDIOVASCULAR SYSTEM, PROCESSES FOR THEIR PREPARATION AND PHARMACEUTICAL COMPOSITIONS CONTAINING THEM

The present invention relates to compounds active on the cardiovascular system and, in particular, it relates to derivatives of 2-amino-1,2,3,4-tetrahydronaphthalene and to their use in therapeutic field.

Various hydroxylated 2-amino-1,2,3,4-tetrahydronaphthalene derivatives are known to be agonists of dopaminergic receptors and several studies about the structure-activity relationship have been carried out to determine the structure characteristics able to ensure the best dopaminergic activity and to avoid, at the same time, the undesired effects of dopamine.

An interesting review of these studies is collected in the paper published by H. E. Katerinopoulos and D. I. Schuster on Drugs of the Future, vol. 12(3), pages 223–253, (1987). In spite of the various studies, however, the topology of deopamin-ergie receptors has not been yet explained and a series of receptor models has been proposed in the last ten years.

In the field of the compounds strictly related to dopamine and/or 2-amino-1,2,3,4-tetrahydponaphthalene, some authors have found that the presence of a $C_3$–$C_4$ alkyl group on the amino function is one of the requirements for dopaminergic activity while the structural requirements of the second substituent on the amino group have not yet been found.

Nevertheless, there ape several examples in literature showing that the structural features of the two substituents on the amino group can be extremely variable, in practice, and that small changes of the molecule can affect both quantitatively and qualitatively the pharmacologic activity in a relevant manner.

Among the most significant examples the following are cited. European patent application No. 0 072 061 (Fisons) describes, among the others, dopamine and amino-1,2,3,4-tetraidronaphthalene derivatives having a mono or di-substituted amino portion of formula

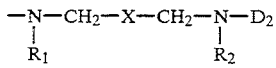

wherein

X is a —$(CH_2)_n$— chain, optionally substituted by hydroxy; n is an integer between 1 and 7; $R_1$ and $R_2$, the same or different, are hydrogen, alkyl or phenyl; $D_2$ is hydrogen, alkyl, phenyl; alkyl substituted by phenyl substituted, in turn, by halogen, alkyl, amino, alkoxy or nitro; or $D_2$ may be the phenylethyl moiety of a dopamine or a hydroxy-1,2,3,4-tetrahydronaphthyl moiety. Among the compounds described in European patent application No. 0 072 061, the compound of formula

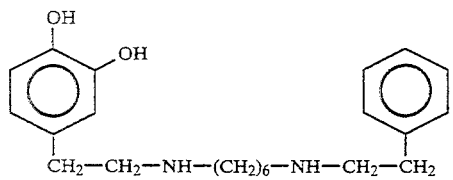

whose international non-proprietary name is dopexamine (The Merck Index - XI Ed., No. 3418, page 538), is the only compound, as far as we know, which has been developed and it is used in therapy in the treatment of acute cardiac insufficiency.

It is significant that dopexamine, not withstanding it was selected among the several compounds described and exemplified in European patent application No. 0 072 061, is an agonist of dopaminergic receptors less active than dopamine and, like dopamine, it is not absorbed when administered by oral route [A. Fitton and P. Benfield, Drugs, 39(2), 308–330, (1990)].

European patent application No. 0 142 283 (Fisons) describes a class of compounds which are analogs of dopexamine and in which the amino group of the dopamine moiety is still secondary.

In literature, there are several examples of compounds, with a catecholamine structure having the aim of keeping the favourable properties of dopexamine, also when administered by opal route, or of increasing the selectivity towards both dopaminergic receptors. As far as we know, however, none of these compounds has shown all the required characteristics.

For the specific treatment of hypertension and of congestire heart failure still exists in the medical class the need of drugs which ape dopaminergic agonists more potent than dopamine but are not selective towards a specific receptor subtype ($D_1$ or $D_2$), which do not interact with other receptor systems, especially $\alpha$, $\beta$ and 5-$HT_2$ receptors, and, contemporaneously, which do not have either the adversed effects or the therapeutic unfavourable aspects of dopamine, such as the lack of absorption by opal route and the short action (Goodman and Gilman's - VII Ed., pages 161–163).

In this connection, it is worth noting European patent application No. 0 321 968 (SIMES Societa Italiana Medicinali e Sintetici S.p.A. now Zambon Group S.p.A.) which describes compounds of formula

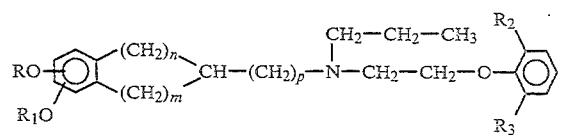

wherein

R and $R_1$, the same or different, are hydrogen atoms or acyl groups derived from optionally substituted aliphatic, aromatic or heteroaromatic carboxylic acids, from optionally substituted carbamic or carbonic acids, or from a phosphoric acid;

n and p are an integer between 0 and 1;

m is an integer selected from 1, 2, 3 and 4 so that n+p=1 and m+n is 2, 3 or 4; $R_2$ and $R_3$, the same or different, are a hydrogen or halogen atom, an alkyl or an alkoxy group.

These compounds are agonists of $D_1$ and $D_2$ dopaminergic receptors, show contemporaneously an $\alpha_1$-antagonist effect, do not interact with other receptor systems, but to be active by oral administration, they must be transformed into suitable pro-drugs.

We have now found agonists of dopaminergic receptors more potent than dopamine, which have substantially no interaction with other receptor systems and, above all, which are absorbed by oral route and have a long duration of action.

Therefore, object of the present invention are the compounds of formula

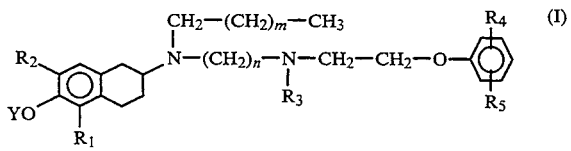

wherein $R_1$ and $R_2$, different from each other, are a hydrogen atom or an OY' group;

Y and Y', the same or different, are a hydrogen atom or an acyl group derived from an optionally substituted aliphatic, aromatic or heteroaromatic carboxylic acid, from an optionally substituted carbamic or carbonic acid or from a phosphoric acid of formula $$R_6-O-\underset{\underset{OH}{|}}{\overset{\overset{O}{\|}}{P}}-$$

wherein $R_6$ is a hydrogen atom, a $C_1$–$C_6$ alkyl optionally substituted by one or more groups selected from hydroxy, alkoxy, acyloxy, amino, carboxy and alkoxycarbonyl; or a phenyl;

m is an integer selected between 1 and 2;

n is an integer from 3 to 7;

$R_3$ is a hydrogen atom or a $C_1$–$C_4$ alkyl;

$R_4$ and $R_5$, the same or different, are a hydrogen or a halogen atom, a $C_1$–$C_3$ alkyl or alkoxy group; and pharmaceutically acceptable salts thereof.

The compounds of formula I have, at least, an asymmetric center and they exist in the form of stereoisomers.

The compounds of formula I in the form of stereoisomeric mixtures as well as of single stereoisomers are object of the present invention. The compounds of formula I are agonists of dopaminergic receptors, are active also by oral route and have a long duration of action and they are useful in therapy in the cardiovascular field, in particular for the treatment of arterial hypertension, congestive heart failure, renal failure, for the treatment of peripheral arteriopathies and in cerebrovascular insufficiencies. Specific examples of alkyl or alkoxy group in the meanings of $R_3$, $R_4$, $R_5$ and $R_6$ are methyl, ethyl, n.propyl, i.propyl, n.butyl, i.butyl, sec.-butyl, ter.butyl, methoxy, ethoxy, n.propoxy and i.-propoxy.

Halogen atoms are fluorine, chlorine, bromine and iodine. The term acyl group derived from an aliphatic carboxylic acid means an acyl radical derived from a linear or branched aliphatic carboxylic acid having from 1 to 6 carbon atoms, optionally substituted by phenyl, halogen or alkoxy groups; specific examples are the acyl groups derived from the following acids: formic, acetic, propionic, butyric, isobutyric, valeric and pivalic; acyl groups from aromatic or heteroaromatic carboxylic acids derive from benzoic or pyridinecarboxylic (2-, 3- or 4-pyridinecarboxylic), pyrrolecarboxylic, isoxazolecarboxylic and quinolinecarboxylic acid, optionally substituted by alkyl, alkoxy, halogen or nitro groups.

Specific examples comprise benzoyl, 2-pyridinecarbonyl, 3-pyridinecarbonyl, 4-pyridinecarbonyl, 2-chlorobenzoyl, 4-chlorobenzoyl, 2-methylbenzoyl, 3-methylbenzoyl, 4-methylbenzoyl, 2,4-dimethylbenzoyl, 4-nitrobenzoyl, 4-isobutyrylbenzoyl, 4-methoxybenzoyl, 2-methoxybenzoyl, 3-methoxybenzoyl.

Preferred substituents for carbamic and carbonic acids are alkyl and phenyl.

Preferred compounds of formula I are the compounds in which $R_1$ is OY', Y, Y' and $R_2$ are hydrogen atoms, n is an integer selected from 5, 6 and 7.

Still more preferred compounds of formula I are the compounds in which $R_1$ is OY', Y, Y' and $R_2$ are hydrogen atoms, n is 6, m is 1, $R_4$ and $R_5$, the same or different, are hydrogen atoms, methyl or methoxy groups, chlorine.

According to the common knowledge in the field of catechol derivatives, the compounds of formula I, wherein at least one among Y and Y' is different from hydrogen, are pro-drugs of the corresponding catechol compound of formula I (Y=Y'=H).

Among the compounds of formula I, preferred pro-drugs are the compounds in which one or both Y and Y', the same or different, are an acyl group derived from acetic, propionic, butyric, isobutyric acid, from optionally substituted benzoic or pyridinecarboxylic acid, from carbamic or carbonic acid.

Pharmaceutically acceptable salts of the compounds of formula I are salts with organic or inorganic acids such as, for example, hydrochloric, hydrobromic, hydriodic, nitric, sulfuric, phosphoric, acetic, aspattic, methansulfonic and 3,7-di-ter.butylnaphthalen-1,5-disulfonic acid (dibudinic acid).

The preparation of the compounds of formula I can be carried out according to the synthetic method described hereinafter.

The method comprises the reaction between a compound of formula

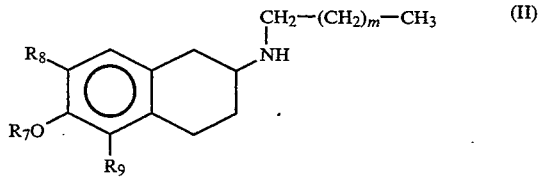

wherein $R_7$ is a hydrogen atom or a protecting group selected, for example, from methyl, benzyl, benzoyl and 4-methoxybenzoyl;

$R_8$ and $R_9$, different from each other, are a hydrogen atom or an —$OR_7$ group;

m has the meanings reported for formula I; and an acid of formula

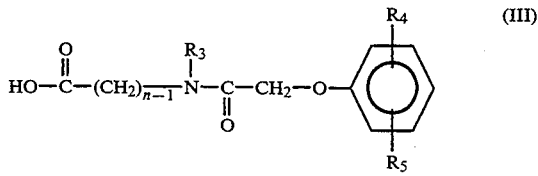

wherein n, $R_3$, $R_4$ and $R_5$ have the meanings reported for formula I; or a reactive derivative thereof such as an acyl halide or a mixed anhydride, optionally prepared "in situ", in an inept solvent and in the presence of a base such as an alkaline carbonate or bicarbonate or a tertiary amine, in order to obtain the intermediate compounds of formula

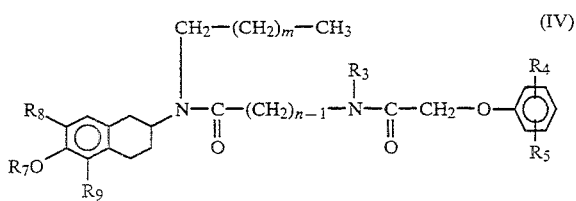

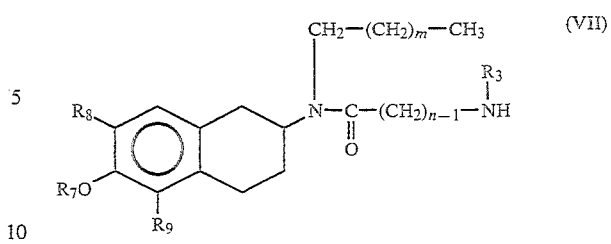

wherein m, n, $R_3$, $R_4$, $R_5$, $R_7$, $R_8$, $R_9$ have the meanings reported for formula II and III; and their reduction, carried out before or after the optional deprotection of the hydroxy groups, in order to obtain the compounds of formula I.

The reduction of the compounds of formula IV can be carried out by using electrophylic reducing agents, in particular diborane optionally complexed with dimethylsulphide, tetrahydrofuran, aliphatic amines such as triethylamine or aromatic amines such as N,N-diethylaniline or pyridine.

Alternatively, the reduction can be carried out with nucleophylic reducing agents such as metal hydride, for example aluminum lithium hydride.

The reduction reaction is carried out in a suitable solvent such as, for example, tetrahydrofuran, diethylether or 1,2-dimethoxyethane. The deprotection, when needed, of the hydroxy groups is carried out according to conventional techniques such as hydrolysis or hydrogenolysis. The compounds of formula II are known or they can be easily prepared according to known methods (British Patent No. 1,509,454 - The Wellcome Foundation Ltd.).

Also the compounds of formula III are known or they can be easily prepared according to conventional methods such as the condensation between an aminoacid of formula

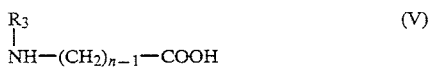

wherein $R_3$ and n have the meanings reported for formula I; and an acyl halide of formula

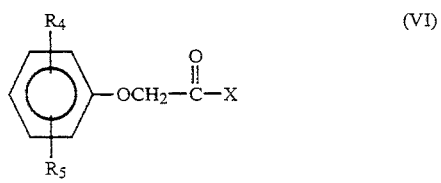

wherein $R_4$ and $R_5$ have the meanings reported for formula I and X is a chlorine or bromine atom.

Alternatively, the synthetic method for the preparation of the compounds of formula I can be carried out by a different sequence of steps.

Therefore, the compounds of formula II can be reacted, first, with an aminoacid of formula V or a reactive derivative thereof, in order to obtain the intermediate of formula where in m, n, $R_3$, $R_7$, $R_8$ and $R_9$ have the meanings reported for formula I and II; which is then acylated with an acyl halide of formula VI, so obtaining the intermediates of formula IV. The subsequent reduction as above reported affords the compounds of formula I, object of the present invention.

The compounds of formula I in optically active form can be obtained by optical separation or by stereospecific or stereoselective synthesis by using an optically active starting compound of formula II. The preparation of the pro-drugs of formula I can be carried out by esterification of one or both the catechol hydroxy groups according to conventional methods.

Before carrying out the esterification reaction it may be useful to protect the secondary (N-$R_3$ when $R_3$=H) amino group, for example as benzyloxycarbonyl derivative.

This protecting group can be easily removed after the esterification, for example by hydrogenolysis.

The preparation of the salts of the compounds of formula I is carried out according to conventional methods.

The compounds of formula I are agonists of $D_1$ and $D_2$ dopaminergic receptors at least 2-10 times more potent than dopamine as shown in the in vitro binding tests (example 11).

In addition, they are also more potent than dopexamine as well as than the compounds described in the above cited European patent application No. 0 321 968.

The tests carried out to evaluate the interaction with other receptor systems have shown that the compounds of formula I do not significantly interact and therefore they are endowed with high specificity.

The compounds of formula I showed to be inactive on the central nervous system and this lack of effect is a further favourable property not shared by other compounds having a catecholamine structure.

It is clear how these characteristics of receptor selectivity and specificity together with the absence of activity on the central nervous system make the compounds of formula I particularly suitable for the treatment of cardiovascular disorders and, mainly, in the antihypertensive therapy, in the therapy of congestive heart failure, of renal failure, in the treatment of peripheral arteriopathies and cerebrovascular insufficiencies.

In addition to the already underlined higher pharmacological activity, the feature that more than others distinguishes the compounds of formula I, object of the invention, is their ability to be absorbed by oral route and their long duration of action (example 12).

As a consequence, for the practical use in therapy, the compounds of formula I can be administered by infusion as well as by enteral route so differing from dopamine and from dopexamine.

The therapeutic doses will be generally between 10 mg and 1 g a day and between 5 and 300 mg by oral route for each administration.

The pharmaceutical compositions containing a therapeutically effective amount of the compounds of formula I or of pharmaceutically acceptable salts thereof in a mixture with a suitable carrier are a further object of the present invention.

The pharmaceutical compositions object of the invention may be liquid, suitable for enteral or parenteral administration or, preferably, solid such as tablets, capsules, granulates, suitable for oral administration.

The preparation of the pharmaceutical compositions can be carried out according to traditional techniques. Some times, in order to meet specific therapeutic or pharmaceutical requirements, in the preparation of the pharmaceutical compositions object of the present invention, it may be more convenient the use of a pro-drug of formula I.

For example, the use of a pro-drug can be useful for improving formulation properties or the compatibility with other active ingredients.

The choice of a compound of formula I in the form of catechol (Y=Y'=H) or of a corresponding pro-drug falls within the technical knowledge of the man skilled in the art.

In order to better illustrate the present invention, the following examples are now given.

EXAMPLE 1

Preparation of (S)-N-propyl-5,6-dimethoxy-1,2,3,4-tetrahydro-2-naphthylamine hydrochloride Method A 10% Palladium on charcoal (50% water) (0.5 g) was added to a solution of (S)-5,6-dimethoxy-1,2,3,4-tetrahydro-2-naphthylamine (50.0 g; 241 mmoles) and propionaldehyde (14.8 g; 255 mmoles) in ethanol 95° (300 ml).

The reaction mixture was kept under stirring and under hydrogen pressure (2.7 atm) at 35° C. for 7 hours.

The catalyst was filtered off and the solvent was evaporated under reduced pressure. The residue was dissolved in absolute ethanol (300 ml) and a solution of hydrochloric acid in ethyl ether (15% w/v) was added up to clearly acid pH.

The precipitate was filtered and dried at 40° C. under vacuum. The title compound was obtained as a white solid (57.6 g). m.p. 257°–262° C.

$^1$H-NMR (300 MHZ, DMSO-$d_6$): δ (ppm): 0.96 (t, 3H); 1.65–1.80 (m, 3H); 2.29 (m, 1H); 2.60 (m, 1H); 2.80–3.00 (m, 4H); 3.13 (dd, 1H); 3.34 (m, 1H); 3.68 (s, 3H) 3.77 (s, 3H); 6.83 (d, 1H); 6.89 (d, 1H). Mass (chemical ionization, isobutane, positive ions): 250 [M+1] By working in a similar way but using butyraldehyde instead of propionaldehyde, and hydrobromic acid instead of hydrochloric acid, the following compound was prepared:
(S)-N-butyl-5,6-dimethoxyl-1,2,3,4-tetrahydro-2-naphthylamine hydrobromide m.p. 226°–228° C.

$^1$H-NMR (200 MHz, CDCl$_3$) (free base): δ (ppm): 0.90 (t, 3H); 1.26–1.62 (m, 5H); 2.05 (m, 1H); 2.60 (m, 2H); 2.69 (m, 2H); 2.81–3.05 (m, 3H); 3.77 (s, 3H); 3.81 (s, 3H); 6.70 (d, 1H); 6.78 (d, 1H).

Mass (chemical ionization, isobutane, positive ions): 264 [M+1]

Method B

Propionyl chloride (14.3 ml; 165 mmoles) was added to a solution of (S)-5,6-dimethoxy-1,2,3,4-tetrahydro-2-naphthylamine (31 g; 150 mmoles) and triethylamine (23 ml; 165 mmoles) in dimethylformamide (310 ml) at room temperature and under nitrogen.

The reaction mixture was kept under stirring for 1 hour, then it was poured into water (1.5 l) and the solid was filtered and washed with water.

After drying at 50° C. under vacuum, (S)-N-propionyl-5,6-dimethoxy-1,2,3,4-tetrahydro-2-naphthylamine (32.8 g) was obtained. m.p. 149°–151° C.

$^1$H-NMR (300 MHz, CDCl$_3$): δ (ppm): 1.14 (t, 3H); 1.70–1.80 (m, 1H); 2.02 (m, 1H); 2.18 (q, 2H); 2.57 (dd, 1H); 2.75–3.00 (m, 2H); 3.04 (dd, 1H); 3.80 (s, 3H); 3.84 (s, 3H); 4.25 (m, 1H); 5.47 (bd, 1H); 6.74 (d, 1H); 6.78 (d, 1H).

Mass (chemical ionization, isobutane, positive ions): 264 [M+1], 190 Borane-dimethylsulphide complex (82 ml/ 854.4 mmoles) was added dropwise to a solution of (S)-N-propionyl-5,6-dimethoxy-1,2,3,4-tetrahydro-2-naphthylamine (22.5 g; 85.4 mmoles), prepared as above described, in anhydrous tetrahydrofuran (900 ml) at room temperature and under nitrogen.

The reaction mixture was heated under reflux for 1.5 hours. After cooling to 15° C., a solution of 36% hydrochloric acid (9.5 ml) in methanol (247 ml) was cautiously added dropwise.

The reaction mixture was heated under reflux for 1 hour, then the solvent (about 500 ml) was distilled off at atmospheric pressure and evaporated to dryness under vacuum.

The resultant crude was dissolved with absolute ethanol and the solution was heated under reflux obtaining, after cooling and filtration, the title compound (23 g) having the same physico-chemical and spectroscopic characteristics reported in method A. By working in a similar way, the following compound was prepared: (S)-N-butyl-5,6-dimethoxy-1,2,3,4-tetrahydro-2-naphthylamine hydrobromide having the same physico-chemical and spectroscopic characteristics reported in method A.

EXAMPLE 2

Preparation of (S)-N-propyl-5,6-dihydroxy-1,2,3,4-tetrahydro-2-naphthylamine hydrobromide A solution of (S)-N-propyl-5,6-dimethoxy-1,2,3,4-tetrahydro-2-naphthylamine hydrochloride (22 g; 76.9 mmoles), prepared as described in example 1, in 48% hydrobromic acid (220 ml) was heated under reflux (about 130° C.) for 3 hours.

The solvent was evaporated to dryness under vacuum; the residue was dissolved with toluene and the solvent was evaporated to dryness. The resultant crude was suspended in ethyl acetate and, after filtration, the title compound (23 g) was obtained.

m.p. 219°–222° C.

$^1$H-NMR (300 MHz, DMSO-$d_6$): δ (ppm): 0.93 (t, 3H); 1.68 (m, 3H); 2.25 (m, 1H); 2.40–2.55 (m, 1H); 2.70–3.10 (m, 5H); 3.31 (m, 1H); 6.40 (d, 1H); 6.61 (d, 1H).

Mass (chemical ionization, isobutane, positive ions): 222 [M+1] By working in a similar way, the following compound was prepared:
(S)-N-butyl-5,6-dihydroxy-1,2,3,4-tetrahydro-2-naphthylamine hydrobromide m.p. 240°–242° C.

$^1$H-NMR (200 MHz, DMSO-$d_6$): δ (ppm): 0.90 (t, 3H); 1.35 (m, 2H); 1.62 (m, 3H); 2.13–3.11 (m, 7H); 3.38 (m, 1H); 6.39 (d, 1H); 6.60 (d, 1H).

Mass (chemical ionization, isobutane, positive ions): 236 [M+1]

EXAMPLE 3

Preparation of (R)-N-propyl-6,7-dihydroxy-1,2,3,4-tetrahydro-2-naphthylamine hydrochloride 10% Palladium on charcoal (50% water) (0.5 g) and triethylamine (2.1 g; 21 mmoles) were added to a solution of (R)-6,7-dihydroxy-1,2,3,4-tetrahydro-2-naphthylamine (5.0 g; 19 mmoles) and propionaldehyde (1.1 g; 19 mmoles) in ethanol 95° (150 ml).

The reaction mixture was kept under stirring and under hydrogen pressure (2.7 atm) at 35° C. for 8 hours.

The catalyst was filtered off and the solvent was evaporated under reduced pressure. The residue was dissolved in absolute ethanol (100 ml) and a solution of hydrochloric acid in ethyl ether (15% w/v) was added up to clearly acid pH. The solvent was evaporated and the crude was purified by chromatographic column on silica gel (230–400 mesh), eluent methylene chloride:methanol:acetec acid=90:10:1.

The title compound (3.8 g) was obtained as a white solid. m.p. 201°–203° C.

$^1$H-NMR (200 MHz, DMSO-d$_6$): δ (ppm): 0.93 (t, 3H); 1.56–1.78 (m, 3H); 2.19 (m, 1H); 2.53–3.02 (m, 6H); 3.30 (m, 1H); 6.46 (s, 2H).

Mass (chemical ionization, isobutane, positive ions): 222 [M+1] By working in a similar way but using butyraldehyde instead of propionaldehyde, the following compound was prepared:

(R)-N-butyl-6,7-dihydroxy-1,2,3,4-tetrahydro-2-naphthylamine hydrochloride
m.p. 126°–128° C.

$^1$H-NMR (200 MHz, DMSO-d$_6$): δ (ppm): 0.89 (t, 3H); 1.34 (m, 2H); 1.54–1.80 (m, 3H); 2.19 (m, 1H): 2.67–2.78 (m, 3H); 2.85–3.10 (m, 3H); 3.42 (m, 1H); 6.45 (s, 2H).

Mass (chemical ionization, isobutane, positive ions): 236 [M+1]

EXAMPLE 4

Preparation of 6-[(2-methoxyphenoxy)acetylamino]hexanoic acid

A solution of (2-methoxyphenoxy)acetyl chloride (24 g; 0.12 moles) in methylene chloride (26 ml) and a solution of sodium hydroxide (4.8 g; 0.12 moles) in water (26 ml) were contemporaneously added dropwise, under vigorous stirring, to a solution of 6-aminohexanoic acid (13.1 g; 0.1 moles) and sodium hydroxide (4 g; 0.1 moles) in water (36 ml).

After 1 hour, the phases were separated and the aqueous phase was washed with methylene chloride, acidified with hydrochloric acid and extracted with methylene chloride. The resultant organic phase was dried on anhydrous sodium sulphate and the solvent was evaporated. The resultant crude was purified by chromatographic column on silica gel (230–400 mesh), eluent methylene chloride:methanol=9:1, obtaining the title compound (20 g).

m.p. 69°–70° C. (ethyl acetate)

$^1$H-NMR (300 MHz, CDCl$_3$): δ (ppm): 1.37 (m, 2H); 1.50–1.70 (m, 4H); 2.33 (t, 2H); 3.33 (m, 2H); 3.88 (s, 3H); 4.55 (s, 2H); 6.90–7.05 (m, 4H); 7.10 (bt, 1H).

Mass (chemical ionization, isobutane, positive ions): 296 8 M+1]By working in a similar way, the following compounds were prepared:

6-[(2-chlorophenoxy)acetylamino]hexanoic acid m.p. 87°–88° C.

$^1$H-NMR (200 MHz, DMSO-d$_6$): δ (ppm): 1.12–1.33 (m, 2H); 1.35–1.56 (m, 4H); 2.18 (t, 2H); 3.12 (m, 2H); 4.58 (s, 2H); 6.98 (m, 2H); 7.31 (dd, 1H): 7.43 (dd, 1H); 7.93 (bt, 1H); 11.98 (bs, 1H). Mass (chemical ionization, isobutane, positive ions): 300 [M+1]

6-[[(2-chloro-4-methyl)phenoxy]acetylamino]hexanoic acid m.p. 92°–95° C.

$^1$H-NMR (200 MHz, DMSO-d$_6$): δ (ppm): 1.12–1.31 (m, 2H); 1.32–1.56 (m, 4H); 2.16 (t, 2H); 2.21 (s, 3H); 3.10 (m, 2H); 4.51 (s, 2H); 6.89 (d, 1H); 7.18 (dd, 1H); 7.26 (dd, 1H); 7.89 (bt, 1H); 12.02 (bs, 1H).

Mass (chemical ionization, isobutane, positive ions): 314 [M+1]

6-[[(2-methoxy-4-methyl)phenoxy]acetylamino]hexanoic acid oil $^1$H-NMR (200 MHz, CDCl$_3$): δ (ppm): 1.24–1.42 (m, 2H); 1.45–1.70 (m, 4H); 2.29 (s, 3H); 2.31 (t, 2H); 3.31 (m, 2H); 3.84 (s, 3H); 4.49 (s, 2H); 6.65–6.80 (m, 3H); 7.08 (bt, 1H).

Mass (chemical ionization, isobutane, positive ions): 310 [M+1]

3-[(2-methoxyphenoxy)acetylamino]propionic acid m.p. 95°–97° C.

$^1$H-NMR (300 MHz, DMSO-d$_6$): δ (ppm): 2.42 (t, 2H); 3.34 (m, 2H); 3.77 and 3.79 (2s, 3H); 4.42 and 4.62 (2s, 2H); 6.80–7.03 (m, 4H); 7.96 (bt, 1H); 12.42 (bs, 1H).

Mass (chemical ionization, isobutane, positive ions): 254 [M+1]

3-[(2-chlorophenoxy)acetylamino]propionic acid m.p. 143°–144° C.

$^1$H-NMR (200 MHz, DMSO-d$_6$): δ (ppm): 2.43 (t, 2H); 3.36 (m, 2H); 4.57 (s, 2H); 6.99 (m, 2H); 7.27 (m, 1H); 7.42 (dd, 1H); 7.98 (bt, 1H); 12.30 (bs, 1H).

Mass (chemical ionization, isobutane, positive ions): 258 [M+1]

3-[[(2-methoxy-4-methyl)phenoxy]acetylamino]propionic acid oil $^1$H-NMR (200 MHz, CDCl$_3$): δ (ppm): 2.28 (s, 3H); 2.72 (t, 2H); 3.69 (m, 2H); 3.82 (s, 3H); 4.50 (s, 2H); 6.63–6.78 (m, 3H); 7.56 (bt, 1H).

Mass (chemical ionization, isobutane, positive ions): 268 [M+1]

EXAMPLE 5

Preparation of 6-[N-methyl-N-[(2-methoxyphenoxy)acetyl]amino]hexanoic acid 1,8-Diazabicyclo[5.4.0]undec-7-ene (DBU) (12.8 g; 84 mmoles) and ethyl 6-bromohexanoate (12.3 g; 55 mmoles) were added under stirring to a solution prepared by bubbling gaseous methylamine into toluene (150 ml) at −10° C. for 20 minutes. The temperature was left arise up to 20° C. The reaction mixture was kept under stirring for 1 hour. The excess of methylamine was removed by bubbling nitrogen under reduced pressure up to neutral pH.

A solution of (2-methoxyphenoxy)acetyl chloride (5.4 g; 27 mmoles) in toluene (10 ml) was added to the reaction mixture under stirring. After 1 hour an aqueous saturated solution of sodium chloride was added and the phases were separated.

The organic phase was dried on anhydrous sodium sulphate and the solvent was evaporated under reduced pressure.

The resultant crude was purified by chromatographic column on silica gel (230–400 mesh), eluent petroleum ether (b.p. 40°–70° C.):ethyl acetate=1:1.

Ethyl 6-[N-methyl-N-[(2-methoxyphenoxy)acetyl]amino]hexanoate (2.6 g) was obtained.

$^1$H-NMR (200 MHz, CDCl$_3$): δ (ppm): 1.23 (t, 3H); 1.30–1.74 (m, 4H); 1.84 (m, 1H); 2.18–2.34 (m, 3H); 2.90 and 3.04 (2s, 3H); 3.30–3.45 (m, 2H); 3.85 (s, 3H); 4.10 (q, 2H); 4.71 (s, 2H); 6.79–6.99 (m, 4H).

Mass (chemical ionization, isobutane, positive ions): 338 [M+1]

A solution of potassium hydroxide (1.1 g; 19.4 mmoles) in water (5 ml) was added to a solution of ethyl 6-[N-methyl-N-[(2-methoxyphenoxy)acetyl]amino]hexanoate (2.5 g; 7.4 mmoles) in methanol (5 ml) under stirring and at room temperature.

The reaction mixture was kept under stirting for 30 minutes, acidified with 1N hydrochloric acid up to pH 1 and the solvent was evaporated to dryness under reduced pressure.

The residue was treated with a mixture of methylene chloride and water. The organic phase was dried on anhydrous sodium sulphate and the solvent was evaporated under reduced pressure.

The resultant crude was purified by chromatographic column on silica gel (230–400 mesh), eluent methylene chloride:methanol:acetic acid=95:5:1.

The title compound (1.8 g) was obtained as an oil.

$^1$H-NMR (200 MHz, CDCl$_3$): δ (ppm): 1.30 (m, 2H); 1.42–1.69 (m, 4H); 2.28 (m, 2H); 2.91 and 3.04 (2s, 3H); 3.30–3.41 (m, 2H); 3.84 (s, 3H); 4.72 (s, 2H); 6.80–6.98 (m, 4H). Mass (chemical ionization, ammonia, positive ions): 310 [M+1] By working in a similar way, the following compounds were prepared:

6 -[N -methyl-N-[[(2-chloro-4-methyl)phenoxy]acetyl]amino]hexanoic acid $^1$H-NMR (200 MHz, CDCl$_3$): δ (ppm): 1.14–1.71 (m, 6H); 2.07 (s, 3H); 2.30 (m, 2H); 2.91 and 3.06 (2s, 3H); 3.37 (m, 2H); 4.71 (s, 2H); 0 6.86 (dd, 1H); 6.96 (dd, 1H); 7.17 (dd, 1H).

Mass (chemical ionization, isobutane, positive ions): 328 [M+1]

3-[N-methyl-N-[(2-methoxyphenoxy)acetyl]amino]propionic acid m.p. 71°–73° C.

$^1$H-NMR (200 MHz, DMSO-d$_6$): δ (ppm): 2.41 and 2.60 (2t, 2H); 2.79 and 3.00 (2s, 3H); 3.50 (m, 2H); 3.75 (s, 3H); 4.72 and 4.81 (2s, 2H); 6.76–6.99 (m, 4H). Mass (chemical ionization, isobutane, positive ions): 268 [M+1]

3-[N-methyl-N-[[(2-chloro-4-methyl)phenoxy]acetyl]amino]propionic acid m.p. 143°–145° C.

$^1$H-NMR (200 MHz, CDCl$_3$): δ (ppm): 2.24 (s, 3H); 2.62 and 2.69 (2t, 2H); 2.93 and 3.14 (2s, 3H); 3.62 and 3.76 (2t, 2H); 4.71 and 4.80 (2s, 2H); 6.85 (t, 1H); 6.96 (dd, 1H); 7.16 (dd, 1H).

Mass (chemical ionization, isobutane, positive ions): 286 [M+1]

EXAMPLE 6

Preparation of S-(−)-N-propyl-N-[6-(2-(2-methoxyphenoxy)ethylamino]hexyl]-5,6-dihydroxy-1,2,3,4-tetrahydro-2-naphthylamine dihydrchloride (Compound 1)

Method A a) Thionyl chloride (68.2 g; 573 mmoles) was added to a solution of 6-[(2-methoxyphenoxy)acetylamino]hexanoic acid (63.5 g; 215 mmoles), prepared as described in example 4, in methylene chloride (420 ml).

After 2 hours at room temperature, the reaction mixture was evaporated to dryness under reduced pressure.

An yellow oil residue was obtained and used in the next step without any further purification.

b) Sodium borate (66.6 8; 331 mmoles) was added under nitrogen to a solution of (S)-N-propyl-5,6-dimethoxy-1,2,3,4-tetrahydro-2-naphthylamine hydrobromide (50.0 g; 165 mmoles), prepared as described in example 2, in water (1000 ml).

The mixture was heated at 70° C. up to complete dissolution, then cooled to room temperature and methylene chloride (100 ml), potassium carbonate (178.3 g; 1.290 moles) and, under vigorous stirring, a solution of the yellow oil residue (prepared as described in the above point a) in methylene chloride (400 ml) were added to the mixture.

After 1 hour at room temperature, toluene (500 ml) was added. After acidification with concentrated hydrochloric acid, the phases were separated. The aqueous phase was extracted again with methylene chloride (500 ml).

The collected organic phases were dried on anhydrous sodium sulphate, filtered and the solvent was evaporated to dryness. The resultant residue was dissolved in tetrahydrofuran (334 ml) under nitrogen and borane-dimethylsulphide complex (172.0 g; 2.143 moles) was slowly added under stirring.

The temperature spontaneously arose up to 35° C. and the reaction mixture was kept at this temperature for 30 minutes, then heated under reflux for 1.5 hours. After cooling to 5° C., a solution of 37% hydrochloric acid (85.2 g; 0.864 mmoles) in methanol (643 ml) was added in 1 hour. The reaction mixture was heated under reflux for 1 hour, concentrated by distilling the solvent (about 750 ml) at atmospheric pressure and then under reduced pressure up to dryness.

The residue was dissolved in methanol (830 ml); the solvent was distilled off under reduced pressure, absolute ethanol (830 ml) was added and the solvent was distilled again. Further absolute ethanol (830 ml) and, then, a solution of hydrochloric acid in ethyl ether (10 ml; 15% w/v) were added.

After evaporation of the solvent, the residue was dissolved in absolute ethanol (660 ml); ethyl acetate (1170 ml) was added and the mixture was cooled at 0°–5° C. for 24 hours.

The crystallized product was filtered and dried at 30° C. under vacuum obtaining Compound 1 as a white solid.

m.p. 193°–194° C. [α]$_D$= −32.5° (1% in methanol)

$^1$H-NMR (300 MHz, DMBO-d$_6$): δ (ppm): 0.92 (t, 3H); 1.34 (bs, 4H); 1.70 (m, 7H); 2.28 (m, 1H); 2.40–2.60 (m, 1H); 2.80–3.20 (m, 9H); 3.30 (t, 2H); 3.50 (m, 1H); 3.76 (s, 3H); 4.25 (t, 2H); 6.41 (d, 1H); 6.62 (d, 1H); 6.85–7.05 (m, 4H). Mass (chemical ionization, isobutane, positive ions): 472 [M+1] By working in a similar way the following compounds were prepared:

(R)-N-propyl-N-[6-[2-(2-methoxyphenoxy)ethylamino]hexyl]-6,7-dihydroxyl-1,2,3,4-tetrahydro-2-naphthylamino dihydrochloride (Compound 2)

$^1$H-NMR (200 MHz, D$_2$O): δ (ppm): 0.78 (t, 3H); 1.19–2.06 (m, 12H); 2.45–3.13 (m, 10 H); 3.30 (m, 2H); 3.38–3.53 (m, 1H); 3.67 (s, 1H); 4.12 (m, 2H); 6.46 (s, 2H); 6.77–6.92 (m, 4H). Mass (chemical ionization, isobutane; positive ions): 471 [M+1](S)-N-butyl-N-[6-[2-(2-methoxyphenoxy)ethylamino]hexyl]-5,6-dihydroxy- 1,2,3,4-tetrahydro-2-naphthylamine dihydrochloride (Compound 3)

¹H-NMR (200 MHz, D₂O): δ (ppm): 0.75 (t, 3H); 1.11–1.67 (m, 12H); 2.16–2.46 (m, 2H); 2.36–3.15 (m, 10H); 3.29–3.34 (m, 2H); 3.41–3.57 (m, 1H); 3.69 (s, 3H); 4.11–4.16 (m, 2H); 6.48 (d, 1H); 6.61 (d, 1H); 6.81–6.93 (m, 4H). Mass (chemical ionization, isobutane, positive ions): 485 [M+1]

(S)-N-butyl-N-[6-[2-2-(chlorophenoxy)ethylamino]hexyl]-5,6-dihydroxy-1,2,3,4-tetrahydro-2-naphthylamine dihydrochloride (Compound 4)

¹H-NMR (200 MHz, D₂O): δ (ppm): 0.74 (t, 3H); 1.11–1.77 (m, 13H); 2.05–2.17 (m, 1H); 2.35–3.57 (m, 13H); 4.17–4.22 (m, 2H); 6.47 (d, 1H); 6.60 (d, 1H); 6.80–7.26 (m, 4H). Mass (chemical ionization, isobutane, positive ions): 489 [M+1]

(S)-N-propyl-N-[6-[2-[(2-chloro-4-methyl)phenoxy]ethylamino]-hexyl]-5,6-dihydroxy-1,2,3,4-tetrahydro-2-naphthylamine dihydrochloride (Compound 5)

¹H-NMR (200 MHz, D₂O): δ (ppm): 0.79 (t, 3H); 1.24–1.75 (m, 11H); 2.04 (s, 3H); 2.03–2.15 (m, 1H); 3.33 (m, 2H); 2.34–3.53 (m, 11H); 4.15 (m, 2H); 6.46 (d, 1H); 6.59 (d, 1H); 6.81 (d, 1H); 6.94 (dd, 1H); 7.04 (d, 1H). Mass (chemical ionization, isobutane, positive ions): 489 [M+1]

(R)-N-propyl-N-[6-[2-[(2-chloro-4-methyl)phenoxy]ethylamino]hexyl]-6,7-dihydroxy-1,2,3,4-tetrahydro-2-naphthylamine dihydrochloride (Compound 6)

¹H-NMR (200 MHz, D₂O): δ (ppm): 0.79 (t, 3H); 1.20–1.69 (m, 10H); 1.47–2.06 (m, 2H); 2.09 (s, 3H); 2.53–3.08 (m, 10H); 3.26–3.31 (m, 2H); 3.40–3.55 (m, 1H); 3.66 (s, 3H); 4.06–4.11 (m, 2H); 6.48 (s, 2H); 6.60–6.77 (m, 3H). Mass (chemical ionization, isobutane, positive ions): 485 [M+1]

(S)-N-propyl-N-[3-[2-[(2-methoxyphenoxy)ethylamino]propyl]-5,6-dihydroxy-1,2,3,4-tetrahydro-2-naphthylamine dihydrochloride (Compound 7)

¹H-NMR (200 MHz, D₂O): δ (ppm): 0.8 (t, 3H); 1.50–2.18 (m, 6H); 2.36–3.23 (m, 10H); 3.35–3.40 (m, 2H); 3.47–3.60 (m, 1H); 3.67 (s, 3H); 4.14–4.19 (m, 2H); 6.48 (d, 1H); 6.61 (d, 1H); 6.83–6.91 (m, 4H).

Mass (chemical ionization, isobutane, positive ions): 429 [M+1]

(R)-N-propyl-N-[3-[2-[(2-chlorophenoxy)ethylamino]propyl]-6,7-dihydroxy-1,2,3,4-tetrahydro-2-naphthylamine dihydrochloride (Compound 8)

¹H-NMR (200 MHz, D₂O): δ (ppm): 0.79 (t, 3H); 1.48–2.14 (m, 6H); 2.46–3.20 (m, 10H); 3.37–3.57 (m, 3H); 4.19–4.24 (m, 2H)6.44 (s, 1H); 6.46 (s, 1H); 6.80–7.25 (m, 4H).

Mass (chemical ionization, isobutane, positive ions): 433 [M+1]

(S)-N-butyl-N-[3-[2-[(2-methoxy-4-methyl)phenoxy]ethylamino]propyl]-5,6-dihydroxyl-1,2,3,4-teyrahydro-2-naphthylamine dihydrochloride (Compound 9)

¹H-NMR (200 MHz, D₂O): δ (ppm): 0.75 (t, 3H) 1.11–1.30 (m, 2H); 1.46–1.62 (m, 2H); 2.08 (s, 3H); 1.60–2.15 (m, 2H); 1.97–2.15 (m, 2H); 2.34–3.22 (m, 10H); 3.31–3.36 (m, 2H); 3.44–3.57 (m, 1H); 3.64 (s, 3H); 4.12 (m, 2H); 6.46 (d, 1H); 6.61 (d, 1H); 6.60–6.78 (m, 3H).

Mass (chemical ionization, isobutane, positive ions): 457 [M+1]

(S)-N-[2-(5,6-dihydroxy-1,2,3,4-tetrahydro)naphthyl]-N-propyl-N'-methyl-N'-[2-(2-methoxyphenoxy)ethyl]-1,6-hexanediamine dihychloride (Compound 10)

¹H-NMR (200 MHz, D₂O): δ (ppm): 0.78 (t, 3H); 1.16–2.07 (m, 12H); 2.76 (S, 3H); 2.26–3.54 (m, 13H); 3.63 (s, 3H); 4.15 (m, 2H); 6.41 (d, 1H); 6.57 (d, 1H); 6.74–6.86 (m, 4H).

Mass (chemical ionization, isobutane, positive ions): 485 [M+1]

(R)-N-butyl-N-[2-(6,7-dihydroxy-1,2,3,4-tetrahydro)-naphthyl]-N'-methyl-N'-[2-(2-methoxyphenoxy)ethyl]-1,6-hexanediamine dihydrochloride (Compound 11)

¹H-NMR (200 MHz, D₂O): δ (ppm): 0.74 (t, 3H); 1.14–1.71 (m, 12H); 1.48–2.04 (m, 2H); 2.77 (s, 3H); 2.54–3.53 (m, 13H); 3.67 (s, H); 4.20 (m, 2H); 6.49 (s, 2H); 6.76–6.93 (m, 4H).

Mass (chemical ionization, isobutane, positive ions): 499 [M+1]

(S)-N-[2-(5,6-dihydroxy-1,2,3,4-tetrahydro)naphthyl]-N-propyl-N'-methyl-N'-[2-[(2-chloro-4-methyl]phenoxyl]ethyl]-1,6-hexanediamine dihydrochloride (Compound 12)

¹H-NMR (200 MHz, D₂O): δ (ppm): 0.79 (t, 3H); 1.22–1.30 (m, 4H); 1.47–1.71 (m, 7H); 2.02 (s, 3H); 2.02–2.13 (m, 1H); 2.80 (s, 3H); 2.32–3.18 (m, 10H); 3.35–3.50 (m, 3H); 4.20 (m, 2H); 6.44 (d, 1H); 6.58 (d, 1H); 6.77–6.99 (m, 3H).

Mass (chemical ionization, isobutane, positive ions): 503 [M+1]

(S)-N-propyl-N-[2-(5,6-dihydroxy-1,2,3,4-tetrahydro)-naphthyl]-N'-methyl-N'-[2-(2-methoxyphenoxy)ethyl]-1,3-propanediamine dihydrochloride (Compound 13)

¹H-NMR (200 MHz, D₂O): δ (ppm): 0.78 (t, 3H); 1.46–2.15 (m, 6H); 2.82 (s, 3H); 2.27–3.51 (m, 13H); 3.61 (s, 3H); 4.22 (m, 2H); 6.42 (d, 1H); 6.60 (d, 1H); 6.74–6.91 (m, 4H).

Mass (chemical ionization, isobutane, positive ions): 443 [M+1]

(R)-N-butyl-N-[2-(6.,7-dihydroxy-1,2,3,4-tetrahydro)-naphthyl]- N'-methyl-N'-[2-[(2-chloro-4-methyl)-phenoxy]ethyl]-1.3-propanediamine dihydrochloride (Compound 14)

¹H-NMR (200 MHz, D₂O): δ (ppm): 0.74 (t, 3H); 1.09–1.28 (m, 2H); 1.44–1.60 (m, 2H); 2.01 (s, 3H); 1.45–2.20 (m, 2H); 1.91–2.20 (m, 2H); 2.88 (s, 3H); 2.40–3.48 (m, 11H); 3.54 (m, 2H); 4.25 (m, 2H); 6.41 (s, 1H); 6.44 (s, 1H); 6.80–6.97 (m, 3H). Mass (chemical ionization, isobutane, positive ions): 475 [M+1]

Method B a) A solution of 4-methoxybenzoylchloride (11.8 g; 69.5 mmoles) in trifluoroacetic acid (24 ml) was added under nitrogen at 20° C. to a solution of (S)-N-propyl-5,6-dihydroxy-1,2,3,4-tetrahydro-2naphthylamine hydrobromide (7 g; 23.2 mmoles), prepared as described in example 2, in trifluoroacetic acid (80 ml). The reaction mixture was kept under stirring at room temperature for 2 hours, then the solvent was evaporated to dryness. The residue was dissolved in ethyl acetate (20 ml) and a solution of hydrochloric acid in diethyl ether was added up to clearly acid pH.

The resultant solid was filtered obtaining (S)-N-propyl-5,6-di-(4-methoxybenzoyloxy)-1,2,3,4-tetrahydro-2-naphthylamine hydrochloride (12.5 g). m.p. 114°–117° C. [α]$_D$ = −42.64° (1% in methanol)

¹H-NMR (300 MHz, DMSO-d₆): δ (ppm): 0.95 (t, 3H); 1.60–1.80 (m, 3H); 2.55 (m, 1H); 2.60 (m, 1H); 2.75–3.05 (m, 4H); 3.31 (dd, 1H); 3.47 (m, 1H); 3.76 (s, 3H); 3.78 (s, 3H); 6.94 (d, 2H); 7.00 (d, 2H); 7.21 (d, 1H);

7.25 (d, 1H); 7.84 (d, 2H); 7.92 (d, 2H). Mass (chemical ionization, isobutane, positive ions): 490 [M+1], 89.

b) Ethylchlorocarbonate (2.9 ml; 27.4 mmoles) was added dropwise at −12° C. under nitrogen to a solution of 6-[(2-methoxyphenoxy)acetylamino]hexanoic acid (8 g; 27.4 mmoles), prepared as described in example 4, and triethylamine (2.8 ml; 27.4 mmoles) in anhydrous dimethylformamide (240 ml).

The reaction mixture was kept under stirring for 30 minutes, keeping the temperature between −10° C. and −12° C., then a solution of (S)-N-propyl-5,6-di-(4-methoxybenzoyloxy)-1,2,3,4-tetrahydro-2-naphthylamine hydrochloride (12 g; 22.8 mmoles), prepared as described in the above point a., and triethylamine (2.3 ml; 22.8 mmoles) in anhydrous dimethylformamide (200 ml) was added. The reaction mixture was kept under stirring overnight at room temperature.

After evaporation to dryness, the residue was dissolved in methylene chloride (100 ml) and washed with water (3×50 ml). The organic phase was dried on anhydrous sodium sulphate and the solvent was evaporated under reduced pressure obtaining (S)-N- -propyl-N-[6-[[(2-methoxyphenoxy)acetyl]amino]hexanoyl]-5,6- -di-(4-methoxybenzoyloxy)-1,2,3,4-tetrahydro-2-naphthylamine as an oil crude (19 g) which was directly used in the next step. $^1$H-NMR (300 MHz, DMSO-d$_6$): δ (ppm): 0.86 (dt, 3H); 1.15-1.35 (m, 2H); 1.35-1.65 (m, 6H); 1.75-2.05 (m, 2H); 2.20-2.40 (m, 2H); 2.70-3.25 (m, 8H); 3.77 (d, 3H); 3.78 (s, 3H); 3.80 (s, 3H); 4.04 (m, 1H); 4.43 (d, 2H); 6.96 (d, 2H); 7.00 (d, 2H); 6.80-7.30 (m, 6H); 7.86 (d, 2H); 7.94 (d, 2H). Mass (chemical ionization, isobutane, positive ions): 767 [M+1], 337, 296.

c) A solution of crude (S)-N-propyl-N-[6-[[(2-methoxyphenoxy)acetyl] amino]hexanoyl]-5,6-di-(4-methoxybenzoyloxy)-1,2,3,4-tetrahydro-2-naphthylamine (18.5 g; 24.15 mmoles), prepared as described in above point b, and butylamine (7.16 ml; 72.5 mmoles) in absolute ethanol (510 ml) was heated under reflux and under nitrogen for 17 hours.

After evaporation to dryness, the resultant crude was purified by chromatographic column on silica gel (230-400 mesh), eluent methylene chloride, then, methylene chloride:methanol=95:5, obtaining (S)-N-propyl-N-[6-[[(2-methoxyphenoxy)acetyl]amino]hexanoyl]-5,6-dihydpoxy-1,2,3,4-tetrahydro-2-naphthylamine (6.3 g) which was directly used in the next step.

To a solution of this compound (60 g; 12.1 mmoles) in anhydrous tetrahydrofuran (240 ml) borane-dimethylsulphide complex (16 ml; 168.5 mmoles) was added dropwise at room temperature under nitrogen.

The reaction mixture was heated under reflux for 1.5 hours. After cooling at 15° C., a solution of 36% hydrochloric acid (3.25 ml) in methanol (45 ml) was cautiously added dropwise. The reaction mixture was heated under reflux for 1 hour, then the solvent (about 120-150 ml) was distilled off at atmospheric pressure and then to dryness under vacuum. The crude was treated twice with methanol by evaporating to dryness each time. The resultant crude was washed with dioxane and then crystallized from absolute ethanol obtaining Compound 1 (4.5 g) having the same physicochemical and spectroscopic characteristics reported in method A.

EXAMPLE 7

Preparation of (S)-N-propyl-N-[6-[2-(2-methoxyphenoxy)ethylamino]-hexyl]-5,6-diacetoxyl-1,2,3,4-tetrahydro-2-naphthylamine dibudinate (Compound 15)

Acetyl chloride (0.4 g; 5.1 mmoles) was added under stirring at room temperature to a solution of Compound 1 (0.9 g; 1.6 mmoles), prepared as described in example 6, in trifluoroacetic acid (7 ml). After 15 hours under these conditions, the solvent was evaporated under reduced pressure and the resultant residue was purified by chromatographic column on silica gel (230-400 mesh), eluent methylene chloride:-methanol=88:12.

The resultant product was dissolved in water (3 ml); a solution of sodium dibudinate (0.5 g; 1.1 mmoles) in water (4 ml) and, then, methylene chloride (5 ml) were added and the phases were separated. The aqueous phase was extracted again with methylene chloride (3 ml).

The collected organic phases were dried on anhydrous sodium sulphate and the solvent was evaporated under reduced pressure. Compound 15 was obtained (0.8 g) as a white solid. m.p. 165°-167° C. (dec.)

H-NMR (200 MHz, D$_2$O): δ (ppm): −0.60 (bs, 2H); 0.36-0.61 (bs, 3H); 0.89 (t, 3H); 1.16 (s, 18H); 1.60 (bs, 3H); 2.24 (s, 6H); 2.08-3.40 (m, 17H); 3.75 (s, 3H); 4.26 (bs, 2H); 6.77-7.10 (m, 6H); 8.05 (s, 2H); 8.67 (s, 2H). Mass (chemical ionization, isobutane, positive ions): 555 [M+1]

EXAMPLE 8

Preparation of (S)-N-propyl-N-[2-(5,6-dihydroxy-1,2,3,4-tetrahydro)-naphthyl]-N'-benzyloxycarbonyl-N'-[2-(2-methoxyphenoxy)ethyl]-1,6-hexanediamine Potassium carbonate (3.4 g; 24.6 mmoles), water (20 ml) and benzylchloroformate (1.3 g; 7.7 mmoles) were added under nitrogen to a solution of Compound 1 (4.0 g; 7.3 mmoles), prepared as described in example 6, in methylene chloride (200 ml) and dimethylformamide (20 ml).

After 1 hour, the reaction mixture was washed twice with an aqueous saturated solution of sodium chloride.

The organic phase was dried on anhydrous sodium sulphate and the solvent was evaporated under reduced pressure. The residue was purified by column chromatography on silica (230-400 mesh), eluent methylene chloride:methanol:toluene:formic acid=90:10:15:0.5, obtaining the title compound (3.6 g) as a white solid.

$^1$H-NMR (200 MHz, CDCl$_3$): δ (ppm): 0.99 (t, 3H); 1.20-1.96 (m, 12H); 2.12-2.20 (m, 1H); 2.75-3.35 (m, 8H); 3.38 (m, 2H); 3.65 (m, 2H); 3.81 (s, 3H); 4.03-4.20 (m, 2H); 5.11 (s, 2H); 6.21 (d, 1H); 6.77 (d, 1H); 6.73-7.38 (m, 9H). Mass (chemical ionization, ammonia, positive ions): 605 [M+1]

EXAMPLE 9

Preparation of (S)-N-propyl-N-[2-(5,6-di-(ethylcarbamoyloxy)-1,2,3,4-tetrahydro)-naphthyl]-N'-benzyloxycarbonyl-N'-[2-(2-methoyphenoxy)-ethyl]-1,6-hexanediamine A solution of (S)-N-propyl-N-[2-(5,6-dihydroxy-1,2,3,4-tetrahydro)naphthyl]-N'-benzyloxycarbonyl-N'-[2-(2-methoxyphenoxy)ethyl]-1,6hexanediamine (3.6 g;

6 mmoles), prepared as described in example 8, in ethylisocyanate (20 ml) was heated at 60° C. under stirring and under nitrogen for 24 hours.

The excess of ethylisocyanate was evaporated under reduced pressure and the residue was dissolved in ethyl acetate. The resultant solution was washed with water.

The organic phase was dried on anhydrous sodium sulphate and the solvent was evaporated under reduced pressure. The residue was purified by column chromatography on silica gel (230–400 mesh), eluent methylene chloride:methanol:toluene=90:5:5, obtaining the title compound (2.2 g).

$^1$H-NMR (200 MHz, CDCl$_3$): δ (ppm): 0.88 (t, 3H); 1.18 (t, 3H); 1.19 (t, 3H); 1.10–1.80 (m, 12H); 1.96–2.18 (m, 1H); 2.40–3.10 (m, 68H); 3.10–3.41 (m, 6H); 3.65 (m, 2H); 3.81 (s, 3H); 4.03–4.21 (m, 5.02–5.17 (m, 2H); 5.11 (s, 2H); 6.72–7.36 (m, 11H).

EXAMPLE 10

Preparation of (S)-N-propyl-N-[6-[2-(2-methoxyphenoxy)ethylamino]-hexyl]-5,6-di-(ethylcarbamoyloxy)-1,2,3,4-tetrahydro-2-naphthylamine (Compound 16)

37% Hydrochloric acid (0.6 ml) and 10% palladium on charcoal (0.2 g) were added to a solution of (S)-N-propyl-N-[2-[5,6-di-(ethylcarbamoyloxy)-1,2,3,4-tetrahydro]naphthyl]-N'-benzyloxycarbonyl-N'-[2-(2-methoxyphenoxy)ethyl]-1,6-hexanediamine (2.0 g; 2.7 mmoles), prepared as described in example 9, in absolute ethanol (80 ml). The reaction mixture was kept under stirring under hydrogen pressure (2.7 atm) at room temperature for 60 hours. The catalyst was filtered off and the solvent was evaporated under reduced pressure.

The residue was purified by column chromatography on silica gel (230–400 mesh), eluent methylene chloride:methanol:toluene:ammonia=80:10:10:0.5, obtaining Compound 16 (0.6 g).

$^1$H-NMR (200 MHz, D$_2$O): δ (ppm): 0.79 (t, 3H); 0.96 (t, 3H); 0.97 (t, 3H); 1.23–1.63 (m, 10H); 1.58–2.13 (m, 2H); 2.37–3.15 (m, 14H); 3.30 (m, 2H); 3.48–3.65 (m, 1H); 3.68 (s, 3H); 4.12 (m, 2H); 6.77–6.97 (m, 6H). Mass (chemical ionization, isobutane, negative ions): 611 [M-1]

EXAMPLE 11

Evaluation of Affinity for D$_1$ and D$_3$ receptors
A) Receptor binding

Brains of male, Sprague-Dawley rats (200–250 g) were removed and membranes from striatal tissues were prepared according to the method described by Billard et al. in Life Sciences, 35, 1885, (1984).

The tissues were homogenized in 50 mM Tris/HCl buffer, pH 7.4 (1:100 weight/volume).

The homogenate was centrifuged and the pellet was resuspended, centrifuged again and resuspended in 50 mM Tris/HCl buffer pH 7.4 containing 120 mM NaCl, 5mM KCl, 2mM CaCl$_2$ and 1 mM MgCl$_2$.

The affinity for D$_1$ receptor and for D$_2$ receptor was evaluated by using [$^3$H]-SCH23390 [B(+)-8-chioro-2,3,4,5-tetrahydro-3-methyl-5-phenyl-1H-3-benzazepine 7-ol hydrochloride] and [$^3$H]-domperidone (The Merck Index - XI Ed., No. 3412, page 537) as labelled ligands respectively.

As reference substances, dopamine and dopexamine were used. The standard incubation conditions (volume 1000 μl) for the assay in which [$^3$H]-SCH23390 was used were as follows: 50 mM Tris/HCl buffer (pH 7.4), 0.2 nM [$^3$H]-SCH23390, a membrane preparation of 130–140 μg proteins/ml.

The mixture was incubated with different concentrations of the tested compounds at 37° C. for 15 minutes, filtered under vacuum through Whatman GF/C filters and then washed 4 times with 5 ml of ice-cold 50 mM Tris/HCl buffer (pH 7.4).

For D$_2$-receptor binding studies [$^3$H]-domperidone (0.3 nM) was incubated in a volume of 1000 μl containing buffer and a membrane preparation as above described. In addition bovine serum albumine (BSA) (0.01%) was added. The mixture was incubated at 37° C. for 30 minutes for each concentration of the tested compounds.

The obtained values, expressed as Ki(nM), for compound 1, dopamine and dopexamine are reported in the following table.

TABLE 1

Affinity [Ki(nM)] for D$_1$ and D$_2$ receptors of Compound 1, dopamine and dopexamine determined by binding studies on rat striatal membranes.

|  | D$_1$ [$^3$H]-SCH23390 | D$_2$ [$^3$H]-domperidone |
|---|---|---|
| Compound 1 | 195 | 4 |
| Dopamine | 1736 | 279 |
| Dopexamine | 2231 | 145 |

Compound 1 showed high affinity for both receptor sub-types being about 10 times more potent than dopamine and dopexamine on D$_1$ receptors and about 100 times more potent on D$_2$ receptors.

B) Receptor binding and DA$_2$-agonist activity

The receptor binding tests to evaluate the affinity for D$_1$ and D$_2$ receptors were repeated according to the method reported in above point A but using [$^3$H]-spiperone (Merck Index - XI Ed., No. 8707, page 1380) as labelled ligand for D$_2$ receptor.

The standard incubation conditions (volume 1 ml) for the assay in which [$^3$H]-SCH23390 was used were as follows: 50 mM Tris/HCl buffer (pH 7.4), 0.2 nM [$^3$H]-SCH23390, a membrane preparation (3 mg/ml corresponding to 130–150 μg proteins/ml), incubation temperature 37° C. and incubation time 15 minutes. The standard incubation conditions (volume 2 ml) for the assay in which [$^3$H]-spiperone was used were as follows: 50 mM Tris/HCl buffer (pH 7.4), 0.2 nM [$^3$H]-spiperone, a membrane preparation (3 mg/ml corresponding to 130–150 μg proteins/ml), incubation temperature 37° C. and incubation time 15 minutes.

The obtained values, expressed as Ki(μM), for compounds 1-1 g, dopamine and dopexamine are reported in table 2. DA$_2$-agonist activity was evaluated as follows. Transversal sections (2–3 mm) of rabbit ear artery were suspended in isolated organ baths containing Krebs-Henseleit solution added with corticosterone (30 μM), desipramine (0.1 μM) and EDTA (10 μM).

The preparation, subjected to a traction of 1 g and to an electric stimulation with field pulses every 5 minutes (10 Hz, 1 msec., 30–60 V, 500 msec. duration) were left stabilize for about 2 hours.

A dose-response curve for the compounds of the invention and for dopamine and dopexamine as reference compounds was determined and the inhibitory effect on the contraction induced by electric stimulation was evaluated.

Each preparation was submitted to three increasing concentrations allowing the recovery of the basal conditions before the subsequent administration.

The obtained values, expressed as pD$_2$(-log EC$_{50}$), for compounds 1-14, dopamine and dopexamine are reported in table 2.

TABLE 2

Affinity [Ki(μM)] for D$_1$ and D$_2$ receptors (receptor binding) on rat striatal membranes and DA$_2$-agonist activity (pD$_2$) on rabbit ear artery for compounds 1-14, dopamine and dopexamine.

| Compound | Binding D$_1$ rat striatum Ki (μM) | Binding D$_2$ rat striatum Ki (μM) | DA$_2$ rabbit ear artery pD$_2$ |
|---|---|---|---|
| Dopamine | 2.2 | 1.3 | 7.40 |
| 1 | 0.09 | 0.0005 | 8.97 |
| 2 | 0.315 | 0.0084 | 8.36 |
| 3 | 0.56 | 0.086 | 7.53 |
| 4 | 0.7 | 0.08 | 6.29 |
| 5 | 0.12 | 0.005 | 8.16 |
| 6 | 0.51 | 0.031 | 7.96 |
| 7 | 1.1 | 0.0011 | 8.67 |
| 8 | 2.65 | 0.016 | 7.35 |
| 9 | 22.0 | 0.19 | 5.98 |
| 10 | 0.41 | 0.0055 | 8.47 |
| 11 | 11.7 | 0.63 | 5.87 |
| 12 | 0.18 | 0.0083 | 6.34 |
| 13 | 3.6 | 0.0098 | 8.39 |
| 14 | 2.8 | 0.26 | 5.22 |
| Dopexamine | 3.2 | 1.7 | 6.35 |

EXAMPLE 12

Evaluation of in vivo antihypertensive activity

Male SHR rats, 3-4 months old, fasted 16 hours before the experiment were used. Systolic blood pressure (SBP) and heart rate (HR) were recorded by tail cuff method in conscious animals by means of a BP Recorder (W+W Basile, Italy). Before every pressure determination animals were maintained at 37° C. for 10 minutes.

SBP and HR values were recorded before and at various times up to seven hours after treatment with the tested compounds.

The compounds were administered orally by gavage, in a volume of 10 ml/kg, at doses between 10 and 160 mg/kg. For the administration, the compounds were suspended in carboxymethylcellulose (CMC) 0.5% in water and additioned with Tween 80 (0.3 ml/10 ml of CMC).

The obtained results, expressed as ED$_{30mmHg}$ (mg/kg p.o.) that is the dose causing a decrease of 30 mmHg from the basal value of SBP (about 15% decrease) are the following:

Compound 1: ED$_{30mmHg}$=22.9 mg/kg p.o.

The results, moreover, show that the effect of the compound 1 was long lasting (about 4 hours).

Similar results were obtained with other compounds of formula I.

What we claim is:

1. A compound of formula

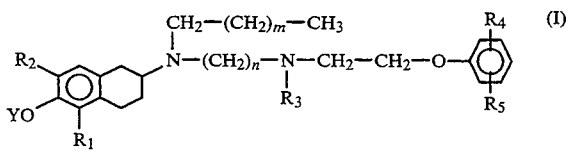

wherein

R$^1$ and R$^2$, different from each other, are a hydrogen atom or an OY' group;

Y and Y', the same or different, are a hydrogen atom or an acyl group derived from an optionally substituted aliphatic, aromatic carboxylic acid, from an optionally substituted carbamic or carbonic acid or from a phosphoric acid of formula

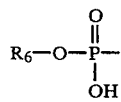

wherein

R$_6$ is a hydrogen atom, a C$_1$-C$_6$ alkyl optionally substituted by one or more groups selected from hydroxy, alkoxy, acyloxy, amino, carboxy and alkoxycarbonyl; or a phenyl;

m is an integer selected between 1 and 2;

n is an integer from 3 to 7;

R$_3$ is a hydrogen atom or a C$_1$-C$_4$ alkyl;

R$_4$ and R$_5$, the same or different, are a hydrogen or a halogen atom, a C$_1$-C$_3$ alkyl or alkoxy group; and pharmaceutically acceptable salts thereof.

2. A compound according to claim 1 in which R$_1$ is OY', Y, Y' and R$_2$ are hydrogen atoms, n is an integer selected from 5, 6 and 7.

3. A compound according to claim 1 in which R$_1$ is OY', Y, Y' and R$_2$ are hydrogen atoms, n is 6, m is 1, R$_4$ and R$_5$, the same or different, are hydrogen atoms, methyl or methoxy groups, chlorine.

4. A compound according to claim 1 in which one or both Y and Y', the same or different, are an acyl group derived from acetic, propionic, buryric, isobutyric acid, from optionally substituted benzoic acid, from carbamic or carbonic acid.

5. A compound according to claim 1 in an optically active form.

6. A pharmaceutical composition containing a therapeutically effective amount of a compound according to claim 1 in admixture with a suitable carrier.

7. S-(−)-N-propyl-N-2-5,6-dihydroxy-1,2,3,4-tetrohydro-2-naphthylamine and salts thereof.

8. A pharmaceutical composition comprising S-(−)-N-propyl-N-5,6-dihydroxy-1,2,3,4-tetrohydro-2-naphthylamine, pharmaceutically acceptable salts thereof and a pharmaceutically acceptable carrier.

* * * * *

UNITED STATES PATENT AND TRADEMARK OFFICE
CERTIFICATE OF CORRECTION

PATENT NO. : 5,407,956
DATED : April 18, 1995
INVENTOR(S) : Francesco SANTANGELO, et al It is certified that error appears in the above-indentified patent and that said Letters Patent is hereby corrected as shown below:

Column 20, Claim 7, "S-(-)-N-propyl-N-2-5,6-dihydroxy-1,2,3,4-tetrohydro-2-naphthylamine" should read --S-(-)-N-propyl-N-[6-[2-(2-methoxyphenoxy)ethylamino]hexyl]-5,6-dihydroxy-1,2,3,4-tetrahydro-2-naphythylamine--.

Claim 8, "S-(-)-N-propyl-N-5,6-dihydroxy-1,2,3,4-tetrohydro-2-naphthylamine," should read --S-(-)-N-propyl-N-[6-[2-(2-methoxyphenoxy)ethylamino]hexyl]-5,6-dihydroxy-1,2,3,4-tetrahydro-2-naphthylamine,--.

Signed and Sealed this

Eleventh Day of July, 1995

Attest:

BRUCE LEHMAN

*Attesting Officer*      *Commissioner of Patents and Trademarks*